(12) United States Patent
Ryono

(10) Patent No.: US 6,395,784 B1
(45) Date of Patent: May 28, 2002

(54) BENZAMIDE LIGANDS FOR THE THYROID RECEPTOR

(75) Inventor: Denis E. Ryono, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/871,347

(22) Filed: May 31, 2001

Related U.S. Application Data

(60) Provisional application No. 60/210,102, filed on Jun. 7, 2000.

(51) Int. Cl.$^7$ .................. A01N 37/12; C07C 229/00
(52) U.S. Cl. .................. 514/563; 514/538; 514/539; 560/39; 560/41; 562/444; 562/449; 562/450
(58) Field of Search .................. 562/444, 449, 562/450; 560/39, 41; 514/563, 538, 539

(56) References Cited

U.S. PATENT DOCUMENTS

| | | |
|---|---|---|
| 5,401,772 A | 3/1995 | Yokoyama et al. |
| 6,194,454 B1 | 2/2001 | Dow |

FOREIGN PATENT DOCUMENTS

| | | |
|---|---|---|
| DE | 1 078 582 | 3/1960 |
| EP | 0580550 | 10/1997 |
| EP | 1088819 | 4/2001 |
| WO | WO 00353 | 1/1999 |
| WO | WO 00/51971 | 8/2000 |
| WO | WO 00/58279 | 10/2000 |

OTHER PUBLICATIONS

Andre et al, "Identification of the Thermal Degradation Products of G–triodothyronine Sodium (Liothyronine Sodium . . . ", Jnl of Chromatography, 725, 1996, 287–294.
Yokoyama et al, "Synthesis and Structure–Activity Relathionships of Oxamic Acid and Acetic Acid Derivative Related to L–Thyronine", J. Med. Che., 38, 1995, 695–707.
Trost et al., "The Thyroid hormone Receptor–beta–selective Agonist GC–1 Differentially Affects Plasma Lipids and Cardiac activity", Endocrinology, V 141, 3057–64 (2000).

*Primary Examiner*—Paul J. Killos
(74) *Attorney, Agent, or Firm*—John M. Kilcoyne

(57) ABSTRACT

New thyroid receptor ligands are provided which have the general formula

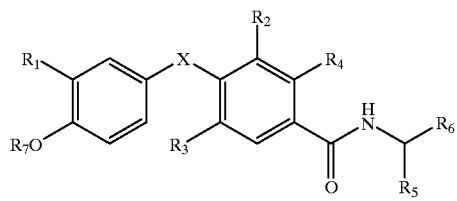

in which:

X is —O—, —S—, —CH$_2$—, —CO—, or —NH—;

R$_1$ is halogen, trifluoromethyl, or alkyl of 1 to 6 carbons or cycloalkyl of 3 to 7 carbons;

R$_2$ and R$_3$ are the same or different and are hydrogen, halogen, alkyl of 1 to 4 carbons or cycloalkyl of 3 to 6 carbons, at least one of R$_2$ and R$_3$ being other than hydrogen;

R$_4$ is methyl, ethyl, n-propyl or trifluoromethyl;

R$_5$ is hydrogen or lower alkyl;

R$_6$ is carboxylic acid, or esters or prodrugs;

R$_7$ is hydrogen or an alkanoyl or an aroyl.

In addition, a method is provided for preventing, inhibiting or treating a disease associated with metabolism dysfunction or which is dependent upon the expression of a T$_3$ regulated gene, wherein a compound as described above is administered in a therapeutically effective amount. Examples of such diseases associated with metabolism dysfunction or are dependent upon the expression of a T$_3$ regulated gene include obesity, hypercholesterolemia, atherosclerosis, cardiac arrhythmias, depression, osteoporosis, hypothyroidism, goiter, thyroid cancer as well as glaucoma, congestive heart failure and skin disorders.

29 Claims, No Drawings

BENZAMIDE LIGANDS FOR THE THYROID RECEPTOR

This application claims priority from U.S. provisional application No. 60/210,102, filed Jun. 7, 2000.

FIELD OF THE INVENTION

This invention relates to novel compounds which are thyroid receptor ligands, and are preferably selective for the thyroid hormone receptor β, and to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. This isoform may be especially important for development. Whereas many mutations in the TRβ gene have been found and lead to the syndrome of generalized resistance to thyroid hormone, mutations leading to impaired TRα function have not been found.

A growing body of data suggest that many or most effects of thyroid hormones on the heart, and in particular on the heart rate and rhythm, are mediated through the α-form of the $TR\beta_1$ isoform, whereas most actions of the hormone such as on the liver, muscle and other tissues are mediated more through the β-forms of the receptor. Thus, a TRβ-selective agonist might not elicit the cardiac rhythm and rate influences of the hormones but would elicit many other actions of the hormones. It is believed that the α-form of the receptor is the major drive to heart rate for the following reasons:

1) tachycardia is very common in the syndrome of generalized resistance to thyroid hormone in which there are defective TRβ-forms, and high circulating levels of $T_4$ and $T_3$;

2) there was a tachycardia in the only described patient with a double deletion of the TRβ gene (Takeda et al, J. Clin. Endrocrinol. & Metab. 1992, Vol. 74, p. 49);

3) a double knockout TRα gene (but not β-gene) in the mouse has a slower pulse than control mice; and, 4) western blot analysis of human myocardial TRs show presence of the $TR\alpha_1$, $TR\alpha_2$ and $TR\beta_2$ proteins, but not $TR\beta_1$.

If these indications are correct, then it may be possible that a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

DESCRIPTION OF THE INVENTION

In accordance with the present invention, compounds are provided which are thyroid receptor ligands, and have the general formula I:

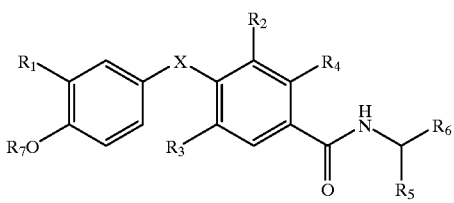

in which:

X is oxygen (—O—), sulfur (—S—), methylene(—CH$_2$—), carbonyl (—CO—), or di-substituted nitrogen (—NH—);

R$_1$ is halogen, trifluoromethyl, or alkyl of 1 to 6 carbons or cycloalkyl of 3 to 7 carbons;

R$_2$ and R$_3$ are the same or different and are hydrogen, halogen, alkyl of 1 to 4 carbons or cycloalkyl of 3 to 6 carbons, at least one of R$_2$ and R$_3$ being other than hydrogen;

R$_4$ is methyl, ethyl, n-propyl or trifluoromethyl;

R$_5$ is hydrogen or lower alkyl;

R$_6$ is carboxylic acid, or an ester thereof (preferably an alkyl ester), or a prodrug thereof;

R$_7$ is hydrogen or an alkanoyl or aroyl (such as acetyl or benzoyl) or other group capable of bioconversion to generate the free phenol structure (wherein R$_7$=H);

including all stereoisomers thereof, prodrug esters thereof, and pharmaceutically acceptable salts thereof.

In addition, in accordance with the present invention, a method for preventing, inhibiting or treating a disease associated with metabolism dysfunction or which is dependent upon the expression of a T$_3$ regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a T$_3$ regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

DETAILED DESCRIPTION OF THE INVENTION

The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "lower alkyl", "alkyl" or "alk" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl, which may be optionally substituted with 1 to 4 substituents which may include alkyl, alkenyl, alkynyl, aryl, cycloalkyl, heteroaryl, hydroxy, cyano, nitro, amino, halo, carboxyl or alkyl ester thereof and/or carboxamide, substituted or unsubstituted.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, hydroxy, amino, nitro, cyano and/or carboxyl or alkyl ester thereof.

The term "heteroaryl" or "heteroaromatic moiety" as used herein alone or as a part of another group refers to a 5- or 6-membered aromatic ring which includes 1, 2, 3, or 4 heteroatoms, one of which must be a nitrogen atom; the other atoms when present may be nitrogen, oxygen or sulfur, and such rings may be fused to another aryl or heteroaryl ring, and includes possible N-oxides. The heteroaryl group may optionally include 1 to 4 substituents such as aryl, alkyl, alkenyl, alkynyl, cycloalkyl, hydroxy, cyano, nitro, amino and/or carboxyl, or alkyl ester thereof.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted as in the case of "alkyl".

Unless otherwise indicated, the term "lower alkynyl" or "alkynyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, which may be substituted as in the case of "alkyl".

The term "alkanoyl" as employed herein alone or as part of another group is alkyl linked to a carbonyl group.

The term "aroyl" as employed herein alone or as part of another group is aryl linked to a carbonyl group.

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, , which may be substituted as in the case of "alkyl".

The term "halogen" or "halo" as used herein alone or as part of another group refers to chlorine, bromine, fluorine, and iodine as well as CF$_3$, with chlorine or bromine being preferred.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–C4) alkyl or arylsulfonic acids which are unsubstituted or substituted, for example by halogen, for example methanesulfonic acid or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic group include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Carboxylic acid prodrugs and prodrugs in general are described in standard references such as Chapter 31, written by Camille G. Wermuth et al., in "The Practice of Medicinal Chemistry", ed. C. G. Wermuth, Academic Press, 1996 (and the references contained therein).

Preferred prodrugs include lower alkyl esters such as ethyl ester, or acyloxyalkyl esters such as pivaloyloxymethyl (POM).

Preferred are compounds of the invention of formula I wherein X=O.

Further preferred compounds are those of formula I wherein X=O;
  $R_1$ is halogen, trifluoromethyl, or alkyl of 1 to 6 carbons;
  $R_2$ and $R_3$ are independently bromo, chloro or methyl;
  $R_4$ is methyl or trifluoromethyl;
  $R_5$ is hydrogen;
  $R_6$ is carboxyl; and
  $R_7$ is hydrogen.

Most preferred compounds of the invention are those of formula I wherein X=O;
  $R_1$ is alkyl of 1 to 6 carbons;
  $R_2$ and $R_3$ are independently bromo, chloro or methyl;
  $R_4$ is methyl;
  $R_5$ is hydrogen;
  $R_6$ is carboxyl; and
  $R_7$ is hydrogen.

Thus, preferred compounds of the invention will have the structures:

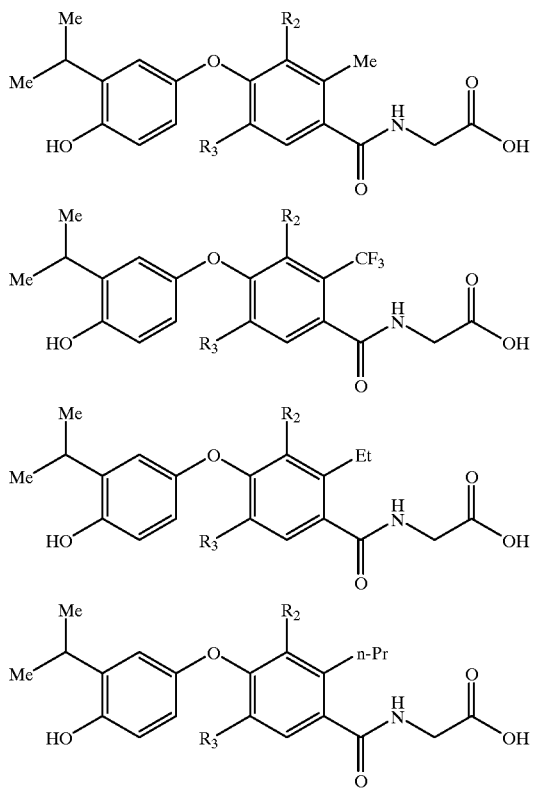

or an alkyl ester thereof.

Preferred compounds have the structures:

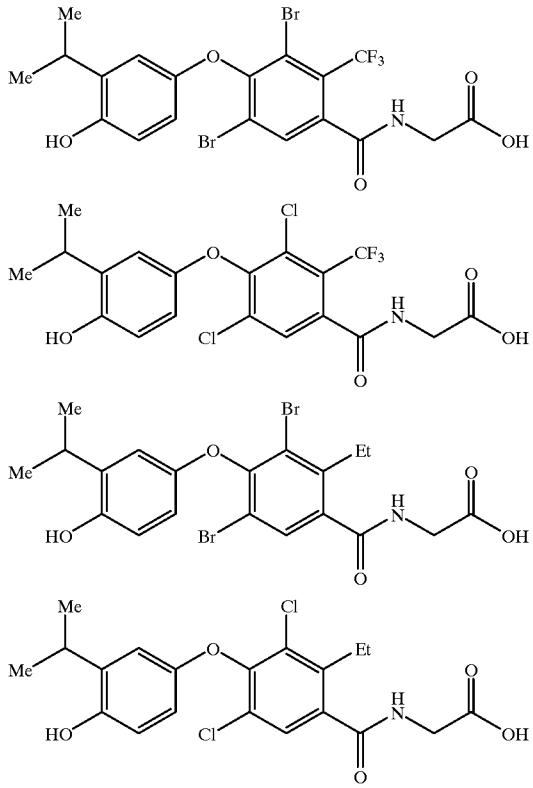

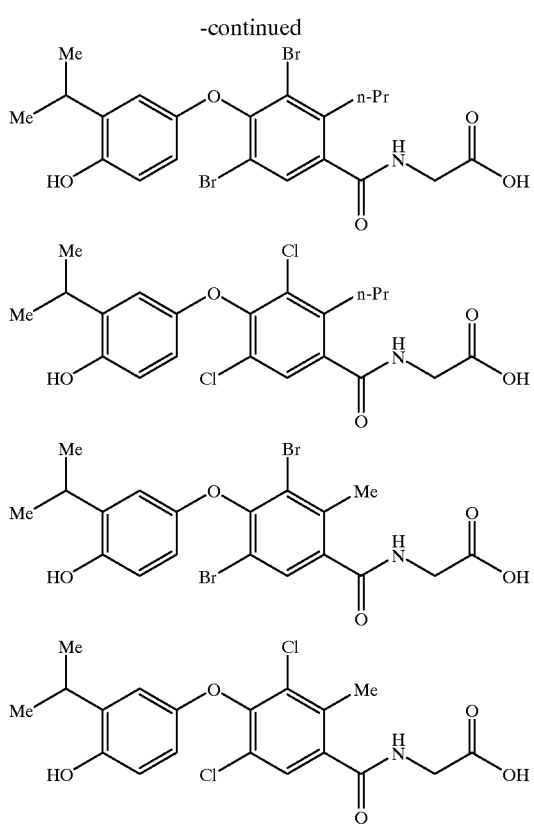

or alkyl esters thereof such as the methyl or ethyl ester thereof.

The most preferred compounds of the invention have the structures:

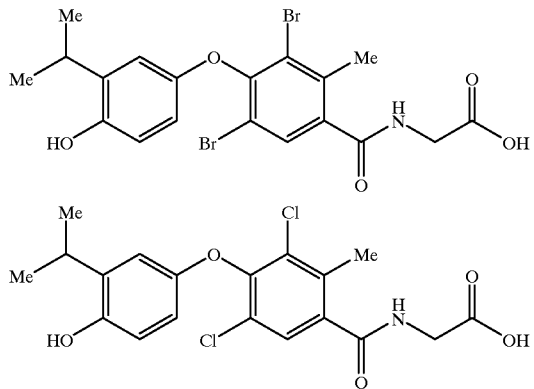

or alkyl esters thereof such as the methyl or ethyl ester.

The compounds of formula I may be prepared by the exemplary processes described in the following reaction schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, "Protecting Groups in Organic Synthesis", 3$^{rd}$ Edition, Wiley, 1999).

Scheme 1 depicts a general synthetic approach to compounds of formula I for which X=O that utilizes the coupling of an appropriately substituted iodonium salt 1 to the appropriate phenol 2 to provide intermediate 3. In structure 1 and all other applicable structures contained in further schemes described below, PG refers to a protecting group appropriate for the functional group indicated (in this instance, for a phenolic oxygen). The specific protecting groups for each particular intermediate are well understood by those versed in the art (see also the reference, "Protecting Groups in Organic Synthesis", cited above). Subsequent protecting group and functional group manipulation provides the desired compounds of formula I. In structures 2 and 3, the group A represents a functional group that is a carboxylic acid or derivative (such as an ester, COOR), or another functional group which can be subsequently converted to a carboxylic acid, and further manipulations provide compounds of formula I. Such functional groups and their means of conversion are well-known to those skilled in the art. For example, A may be a formyl group (CHO) which can be oxidized to a carboxylic acid (COOH) by the use any one of many known oxidizing agents capable of effecting such a transformation.

Scheme 1

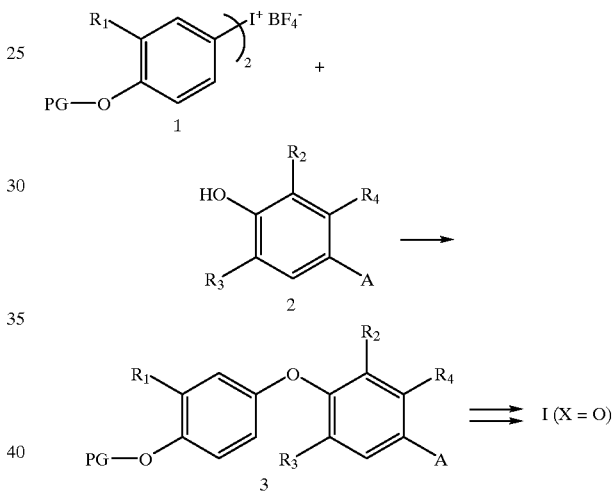

The iodonium salt methodology depicted in Scheme 1 is amply described in the literature for the synthesis of thyroid hormone analogs ("Novel Thyroid Receptor Ligands and Methods, Y.-L. Li, Y. Liu, A. Hedfors, J. Malm, C. Mellin, M. Zhang, PCT Int. App. Wo 9900353 Al 990107; D. M. B. Hickey et al., J. Chem. Soc. Perkin Trans. I, 3103–3111, 1988; N. Yokoyama et al., J. Med. Chem., 38, 695–707, 1995), and to diaryl ethers in general (E. A. Couladouros, V. I. Moutsos, Tetrahedron Lett., 40, 7023–7026, 1999).

Scheme 2 depicts another general synthetic approach to compounds of formula I for which X=O in which an appropriately substituted phenol 4 is alkylated with an appropriately substituted intermediate 5 (for which Y is fluoro, chloro, iodo or bromo) to provide the intermediate 6. In structures 5 and 6, the group B represents a functional group such as nitro or formyl that is capable of activating the aryl halide (Y=F, I, Br or Cl) to displacement. The activating-group B is then subsequently transformed to a carboxylic acid or derivative which can then be further converted to compounds of formula I for which X=O. Such functional groups and their means of conversion are well-known to those skilled in the art. For example, when B is a nitro function in intermediate 6, the nitro group can be reduced to an amino group by methods well known in the art, such as the use of catalytic hydrogenation in the presence of, for example, Raney nickel or palladium on charcoal catalyst, in a polar solvent such as glacial acetic acid or ethanol. Alternatively, the reduction can be accomplished using iron powder in aqueous glacial acetic acid at ambient temperatures. The resulting aryl amine can be converted to the corresponding diazonium salt by the use, for example, of a mixture of sodium nitrite and sulfuric acid in appropriate solvents. The resulting diazonium group can then be converted to a formyl group (CHO) by the reaction with carbon monoxide catalzyed by an appropriate palladium catalyst such as palladium acetate. Subsequent protecting group and functional group manipulation provides the desired compounds of formula I in which X=O.

Scheme 2

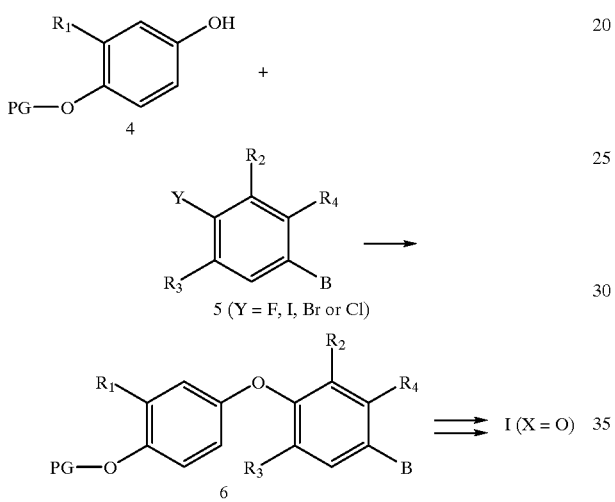

The approach depicted in Scheme 2 for the general synthesis of diaryl ethers for thyromimetics is well precedented in the literature (P. D. Leeson, J. C. Emmett, J. Chem. Perkin Trans. I, 3085–3096, 1988; N. Yokoyama et al., J. Med. Chem., 38, 695–707, 1995).

Further means for synthesizing compounds of formula I in which X=O, NH, S, CO or $CH_2$ are generally described in the literature (for X=O: D. M. B. Hickey et al., J. Chem. Soc. Perkin Trans. I, 3097–3102, 1988; Z.-W. Guo et al., J. Org. Chem., 62, 6700–6701, 1997; D. M. T. Chan et al., Tetrahedron Lett., 39, 2933–2936, 1998; D. A. Evans et al., Tetrahedron Lett., 39, 2937–2940, 1998; G. M. Salamonczyk et al., Tetrahedron Lett., 38, 6965–6968, 1997; J.-F. Marcoux, J. Am. Chem. Soc., 119, 10539–10540, 1997; A. V. Kalinin et al., J. Org. Chem., 64, 2986–2987, 1999; for X=N: D. M. T. Chan et al., Tetrahedron Lett., 39, 2933–2936, 1998; J. P. Wolfe et al., J. Am. Chem. Soc., 118, 7215, 1996; M. S. Driver, J. F. Hartwig, J. Am. Chem. Soc., 118, 7217, 1996; see references in the review by C. G. Frost, P. Mendonca, J. Chem. Soc. Perkin I, 2615–2623, 1998; for X=S: C. R. Harrington, Biochem. J., 43, 434–437, 1948; A. Dibbo et al., J. Chem. Soc., 2890–2902, 1961; N. Yokoyama et al., U.S. Pat. No. 5,401,772, 1995; for X=CO or $CH_2$: L. Horner, H. H. G. Medem, Chem. Ber., 85, 520–530, 1952; G. Chiellini et al., Chemistry & Biology, 5, 299–306, 1998).

Methods applicable to the synthesis of compounds of formula I in which X=O and $R_2$ and $R_3$ are independently varied as hydrogen, halogen and alkyl are described in "Novel Thyroid Receptor Ligands and Methods, Y.-L. Li, Y. Liu, A. Hedfors, J. Malm, C. Mellin, M. Zhang, PCT Int. App. WO 9900353 A1 990107.

Scheme 3 shows an example of the approach described in Scheme 1 wherein the group A is a carboxylic ester function and $R_2 = R_3 = Br$, Cl or I. Readily available meta-OH substituted alkyl benzene compounds can be acetylated to give the intermediate O-acetyl phenol 7 which undergoes a Fries rearrangement (Shine, "Aromatic Rearrangements", American Elsevier, 72–82, 365–368, 1967) to provide the acetophenone intermediate 8. Intermediate 8 is converted to carboxylic acid 9 using the haloform reaction (Chakrabarty, "Oxidation in Organic Chemistry", part C, ed. Trahanovsky, Academic Press, New York, 343–370, 1978). Esterification of acid 9 to methyl ester 10 is accomplished by standard means (such as the use of methanol saturated with HCl). Alternatively, other ester protecting groups can be used. The resulting ester 10 is coupled to iodonium salt 11 to give the diphenyl ether intermediate 12. Conversion of the ester group back to the carboxylic acid is followed by coupling to an amine $HNR_5R_6$ using standard reagents such as dicyclohexylcarbodiimide with HOAt catalyst to give, after removal of protecting groups, the compound of formula I in which $R_2=R_3=Br$, Cl or I.

Scheme 3

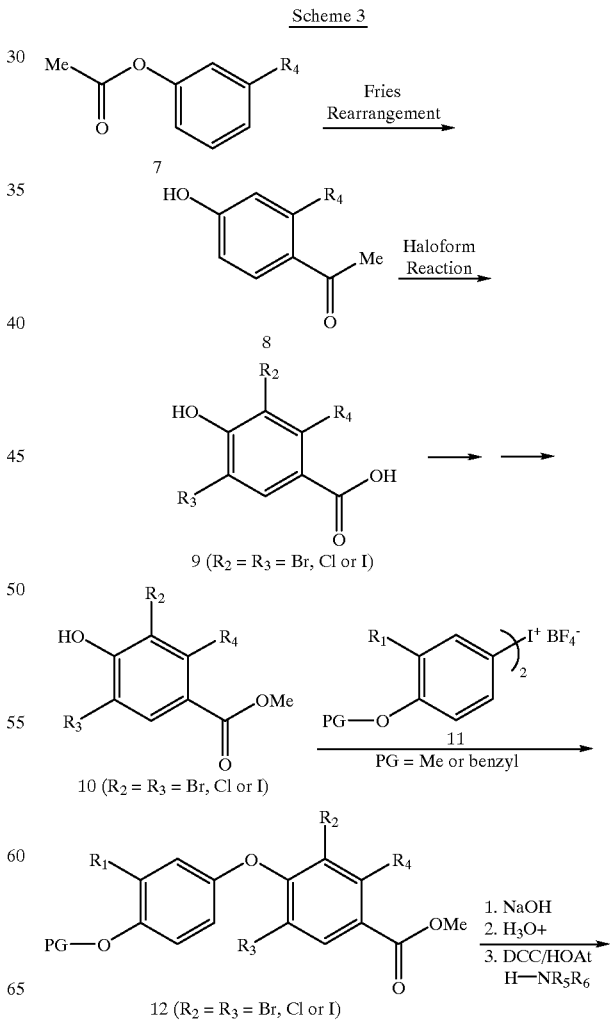

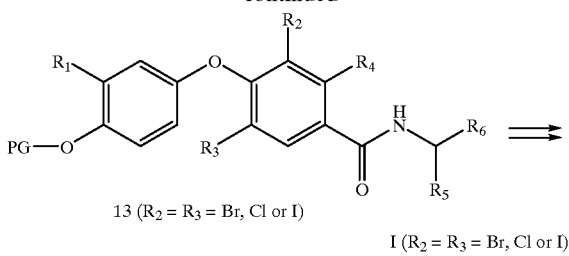

13 (R$_2$ = R$_3$ = Br, Cl or I)

I (R$_2$ = R$_3$ = Br, Cl or I)

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the invention are agonists, that are preferably selective for the thyroid hormone receptor-beta, and as such are useful in the treatment of obesity, hypercholesterolemia and atherosclerosis by lowering of serum LDL levels, alone or optionally in combination with a lipid modulating drug such as an HMG-CoA reductase inhibitor, fibrate, MTP inhibitor, squalene synthetase inhibitor and/or other hypolipidemic agent and/or optionally in combination with an antidiabetic agent; useful in the amelioration of depression, alone or optionally in combination with an antidepressant such as fluoxetine and desipramine; and useful in the stimulation of bone formation to treat osteoporosis, alone or optionally in combination with any known bone resorption inhibitor such as alendronate sodium. In addition, the compounds of the invention may be useful as replacement therapy in elderly patients with hypothyroidism or subclinical hypothyroidism who are at risk for cardiovascular complications, in the treatment of the elderly to provide a sense of well-being, and in the treatment of non-toxic goiter; in the management of papillary or follicular thyroid cancer (alone or with T4); in the treatment of skin disorders such as psoriasis, glaucoma, cardiovascular disease such as in the prevention or treatment of atherosclerosis, and congestive heart failure.

The compounds of the invention may be employed alone or in combination with an appetite suppressant such as sibutramine, and/or in combination with anti-obesity agents such as orlistat, and/or in combination with a β3 agonist, for treating obesity.

The compounds of the invention may also be used to treat skin disorders or diseases involving dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both the glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

In treating skin disorders or diseases as described above, the compounds of the invention may be used alone or optionally in combination with a retinoid such as tretinoin or a vitamin D analog, employing amounts as disclosed in the PDR.

The hypolipidemic agent which may be optionally employed in combination with the compounds of formula I of the invention may include thiazolidinediones, MTP inhibitors, HMG CoA reductase inhibitors, squalene synthetase inhibitors, fibric acid derivatives, ACAT inhibitors, cholesterol absorption inhibitors, ileal Na$^+$/bile acid cotransporter inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl] butyl]-N-(2,2,2-trifluoroethyl)-9H-fluorene-9-carboxamide

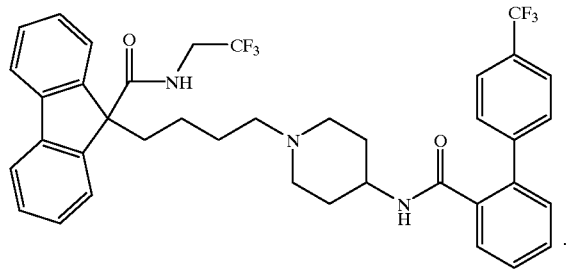

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171.Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2- hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinylmethyl) phosphonates as well as other squalene synthetase inhibitors as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin and cerivastatin.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolypidemic agent, the antidepressant, and/or bone resorption inhibitor and/or appetite suppressant (where present), within the range from about 500:1 to about 0.005:1, preferably from about 300:1 to about 0.01:1.

The antidiabetic agent which may be optionally employed in combination with compounds of formula I of the invention may include biguanides, sulfonyl ureas, glucosidase inhibitors, thiazolidinediones and/or aP2 inhibitors and/or PPAR α agonists, PPAR γ agonists or PPAR α/γ dual agonists, and/or SGLT2 inhibitors, or meglitinide.

The antidiabetic agent may be an oral antihyperglycemic agent preferably a biguanide such as metformin or phenformin or salts thereof.

Where the antidiabetic agent is a biguanide, the compounds of structure I will be employed in a weight ratio to biguanide within the range from about 0.01:1 to about 100:1, preferably from about 0.5:1 to about 2:1.

The antidiabetic agent may also preferably be a sulfonylurea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The compounds of structure I will be employed in a weight ratio to the glucosidase inhibitor within the range from about 0.01:1 to about 100:1, preferably from about 0.5:1 to about 50:1.

The compounds of structure I may be employed in combination with a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GI-262570, englitazone (CP-68722, Pfizer), or darglitazone (CP-86325, Pfizer).

The compounds of structure I will be employed in a weight ratio to the thiazolidinedione in an amount within the range from about 0.01:1 to about 100:1, preferably from about 0.5:1 to about 5:1.

The sulfonylurea and thiazolidinedione in amounts of less than about 150 mg oral antidiabetic agent may be incorporated in a single tablet with the compounds of structure I.

The compounds of structure I may also be employed in combination with a non-oral antihyperglycemic agent such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference), which may be administered via injection, intranasal, or by transdermal or buccal devices.

Where present, metformin, the sulfonylureas, such as glyburide, glimepiride, glipyride, glipizide, chlorpropamide and gliclazide and the glucosidase inhibitors acarbose or miglitol or insulin may be employed in formulations as described above and in amounts and dosing as indicated in the Physician's Desk Reference.

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent may also be a PPAR α/γ dual agonist such as disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an aP2 inhibitor such as disclosed in U.S. application Ser. No. 09/391,053, filed Sep. 7, 1999, and U.S. provisional application No. 60/127,745, filed Apr. 5, 1999 (attorney file LA27*), employing dosages as set out herein.

The antidiabetic agent may be an SGLT2 inhibitor such as disclosed in U.S. provisional application 60/158,773 filed Oct. 12, 1999 (Attorney file LA0049*).

The compounds of formula I will be employed in a weight ratio to the PPAR α agonist, PPAR γ agonist, PPAR γ/α dual agonists, SGLT2 inhibitor and/or aP2 inhibitor within the range from about 0.01:1 to about 100:1, preferably from about 0.5:1 to about 5:1.

The dose administered must be carefully adjusted according to age, weight and condition of the patient, as well as the route of administration, dosage form and regimen and the desired result.

The dosages and formulations for the hypolipidemic agent and antidiabetic agent will be as disclosed in the various patents and applications discussed above and in the PDR.

The dosages and formulations for the other hypolipidemic agent, antidepressant, bone resorption inhibitor, appetite suppressant and anti-obesity agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The compounds of formula I and the hypolipidemic agent, antidepressant or bone resorption inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The compounds of formula I of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, ointment, hydrophilic ointment, cream, lotion, solution or suspension or in other type carrier materials such as transdermal devices, iontophoretic devices, rectal suppositories, inhalant devices and the like. The composition or carrier will contain about 5 to about 500 mg per unit of dosage of a compound of formula I. They may be compounded in conventional matter with a physiologically acceptable vehicle or carrier, excipient, binder, preservative, stabilizer, and flavor, as called for by accepted pharmaceutical practice.

The following working Examples represent preferred embodiments of the present invention.

EXAMPLE 1

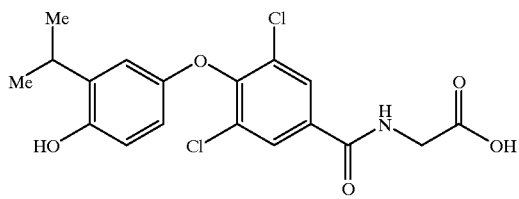

N-[3,5-Dichloro-4-[4-hydroxy-3-(1-methylethyl)phenoxy]benzoyl]glycine

Compound 1A:

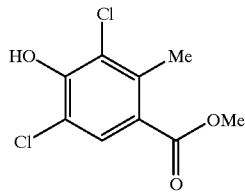

[From P. F. Juby et al., J. Med. Chem., 11, 111–117, 1968; and P. F. Juby, U.S. Pat. No. 3,294,813]

To a solution of sodium hypochlorite (120 mL) in $H_2O$ (150 mL) cooled with an ice-water bath was added 4'-hydroxy-2'-methylacetophenone. After 30 min of cooling, the mixture was allowed to stir at RT for 30 min, and then it was heated to 40° C. and maintained at this temperature for an hour. A solution of $NaHSO_3$ (10 g in 100 mL $H_2O$) was added to the mixture. The mixture was acidified to pH 2 with concentrated HCl. The precipitates formed were filtered off. The wet filter cake was taken up in EtOAc (400 mL) and then washed with brine (2×100 mL). The EtOAc extract was dried ($Na_2SO_4$), filtered, concentrated and dried in vacuo to give 8.826 g of crude 3,5-dichloro-4-hydroxy-2-methylbenzoic acid as a yellow solid (78% desired product by analytical HPLC analysis).

A solution of the crude 3,5-dichloro-4-hydroxy-2-methylbenzoic acid (1.5 g) in methanolic HCl (50 mL) was heated to 80° C. and maintained at this temperature overnight (ca. 15 h). The mixture was cooled down to RT and concentrated in vacuo. The crude product was purified by chromatography (100 g silica gel, 20% EtOAc in hexane as eluent) to give 1.1033 g of purified methyl ester as product (69% yield for the two steps).

$^1$H NMR (500 MHz, $CDCl_3$, δ) 7.89 (s, 1H), 6.23 (s, 1H), 3.87 (s, 3H), 2.65 (s, 3H). MS ESI$^-$ [MH]$^-$=233, 235, 237 (100:64:10).

Compound 1B:

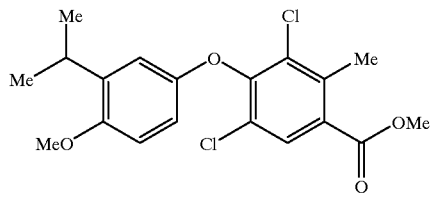

To a stirring mixture of bis(3-isopropyl-4-methoxyphenyl)iodonium tetrafluoroborate (4.36 g, 8.51 mmol) and copper (0.54 g, 8.50 mmol) in $CH_2Cl_2$ (10 mL) was added a solution of compound 1A (1.00 g, 4.25 mmol) and triethylamine (1.2 mL, 0.87 g, 8.61 mmol) in $CH_2Cl_2$ (10 mL). The mixture was stirred at ambient RT in the dark for 3 days under $N_2$. The mixture was filtered through a short pad of celite. The filtrate was concentrated in vacuo. The crude product was purified by chromatography (250 g of silica gel, 3% EtOAc in hexane as eluent) to give 1.56 g (95%) of desired product as a white solid.

$^1$H NMR (500 MHz, $CDCl_3$, δ) 7.89 (s, 1H), 6.845 (d, 1H, J=3.3 Hz), 6.68 (d, 1H, J=8.8 Hz), 6.395 (dd, 1H, J=8.8, 3.3 Hz), 3.92 (s, 3H), 3.77(s, 3H), 3.27 (septet, 1H, J=7 Hz), 2.64 (s, 3H), 1.165 (d, 6H, J=7.1 Hz).

Compound 1C:

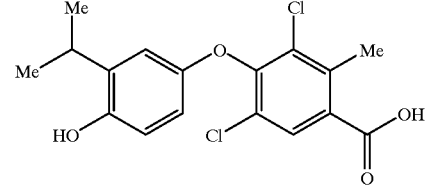

To a solution of compound 1B (0.88 g, 2.30 mmol) in anhydrous $CH_2Cl_2$ (23 mL) cooled with an ice-$H_2O$ bath was added boron tribromide (5.83 g, 2.2 ml, 23.27 mmol). The mixture was allowed to warm up to RT. After 2 h, the mixture was slowly poured into a flask containing ice-$H_2O$ (100 mL). After 15 min of stirring, EtOAc (100 mL) was added. The organic layer was separated and the $H_2O$ layer was extracted with EtOAc (50 mL). The combined organic extracts were washed with brine (100 mL), dried ($Na_2SO_4$), filtered, concentrated and dried in vacuo to give 0.83 g of slightly brownish solid product (94% pure by HPLC analysis).

$^1$H NMR (500 MHz, $CD_3OD$, δ) 7.91 (s, 1H), 6.665 (d, 1H, J=3.3 Hz), 6.62 (d, 1H, J=8.8 Hz), 6.295 (dd, 1H, J=8.8, 3.3 Hz), 3.23 (septet, 1H, J=7 Hz), 2.63 (s, 3H), 1.155 (d, 6H, J=7.1 Hz). LC MS ESI$^-$ [M-H]$^-$=353, 355, 357 (100:64:10).

Compound 1D:

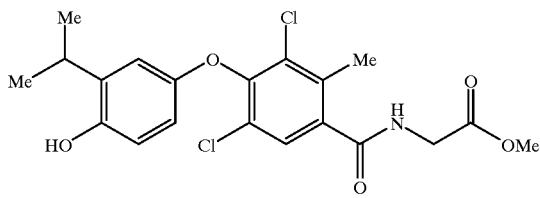

To a stirring mixture of compound 1C (0.83 g, 2.34 mmol), methyl glycine ester hydrochloride (0.58 g, 4.62 mmol), 1-[3-(dimethylamino)propyl]-3-ethylcarbodiimide hydrochloride (0.66 g, 3.44 mmol) and 1-hydroxybenzotriazole (0.46 g, 3.44 mmol) in $CH_2C_{22}$ (20 mL) and DMF (3 mL) cooled with an ice-$H_2O$ bath was added N-methylmorpholine (0.55 g, 0.6 mL, 5.46 mmol). The mixture was allowed to warm up to RT and left to stir overnight (ca. 18 h) under $N_2$. $CH_2cl_2$ was removed in vacuo and the residue was taken up in EtOAc (75 mL) and $H_2O$ (25 mL). The EtOAc extract was washed successively with 1N HCl (2×50 mL), saturated aqueous $NaHCO_3$ (2×50 mL), and brine (2×50 mL). The EtOAc extract was dried ($Na_2SO_4$), filtered and concentrated in vacuo to give 1.17 g of crude product as an orange solid. The crude product was purified by chromatography (50 g silica gel, 40% EtOAc in hexane) to give 0.87 g (88.7% yield) of slightly pinkish solid as purified product.

$^1$H NMR (500 MHz, $CDCl_3$, δ) 7.44 (s, 1H), 6.825 (d, 1H, J=3.3 Hz), 6.60 (d, 1H, J 8.8 Hz), 6.325 (dd, 1H, J=8.8, 3.3 Hz) 6.30 (t, 1H, J=5 Hz), 4.76 (s, 1H), 4.235 (d, 2H, J=5.5 Hz), 3.82 (s, 3H), 3.16 (septet, 1H, J=7 Hz), 2.47 (s, 3H), 1.225 (d, 6H, J=7.1 Hz).

$^{13}$C NMR (8) 170.00, 167.95, 150.74, 149.03, 148.19, 136,22, 135.47, 134.27, 131.94, 126.99, 126.82, 115.64, 114.00, 111.98, 52.66, 41.61, 27.39, 22.39, 17.34 MS ESI$^-$ [M-H]$^-$=424, 426, 428 (100:64:10).

EXAMPLE 1

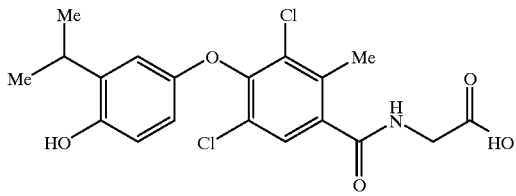

To a solution of compound 1D (0.8 g, 1.88 mmol) in THF (12 mL) was added 1N aqueous lithium hydroxide solution (6 mL, 6 mmol). After 2 h, the mixture was acidified with 1N HCl and then extracted with EtOAc (75 mL). The EtOAc extract was washed with brine (2×25 mL), dried ($Na_2SO_4$), filtered, concentrated and dried in vacuo to give 0.71 g of example 1 (92% yield).

$^1$H NMR (500 MHz, $CD_3OD$, δ) 7.53 (s, 1H), 6.645 (d, 1H, J=3.3 Hz), 6.62 (d, 1H, J=8.8 Hz), 6.335 (dd, 1H, J=8.8, 3.3 Hz), 4.07 (s, 2H), 3.25 (septet, 1H, J=7 Hz), 2.46 (s, 3H), 1.145 (d, 6H, J=7.1 Hz) $^{13}$C NMR (δ) 172.59, 170.91, 151.39, 150.91, 150.10, 137.57, 136.44, 132.52, 128.34, 127.98, 116.36, 114.06, 113.15, 42.09, 28.21, 22.88, 17.45. MS ESI$^-$ [M-H]$^-$=410, 412, 414 (100:64:10)

EXAMPLES 2–28

By appropriate application of the procedures described above combined with those described for analogous examples found in "Novel Thyroid Receptor Ligands and Methods, Y.-L. Li, Y. Liu, A. Hedfors, J. Malm C. Mellin, M. Zhang, PCT Int. App. WO 9900353 A1 9901077, the Examples 2–28 described in the table below are prepared.

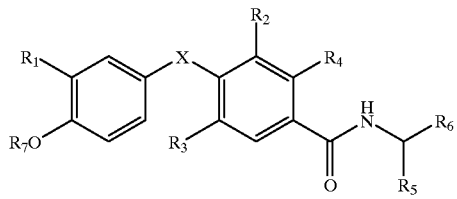

| Ex. | R1 | R2 | R3 | R4 | R5 | R6 | R7 |
|---|---|---|---|---|---|---|---|
| 2 | i-Pr | Me | Me | Me | H | COOH | H |
| 3 | i-Pr | Me | Br | Me | H | COOH | H |
| 4 | i-Pr | Me | Cl | Me | H | COOH | H |
| 5 | i-Pr | Me | I | Me | H | COOH | H |
| 6 | i-Pr | Br | Cl | Me | H | COOH | H |
| 7 | i-Pr | Br | I | Me | H | COOH | H |
| 8 | i-Pr | Br | Br | Me | H | COOH | H |
| 9 | i-Pr | Cl | I | Me | H | COOH | H |
| 10 | i-Pr | I | I | Me | H | COOH | H |
| 11 | i-Pr | H | Me | Me | H | COOH | H |
| 12 | i-Pr | H | Br | Me | H | COOH | H |
| 13 | i-Pr | H | Cl | Me | H | COOH | H |
| 14 | i-Pr | H | I | Me | H | COOH | H |
| 15 | i-Pr | Cl | Cl | CF3 | H | COOH | H |
| 16 | i-Pr | Br | Br | CF3 | H | COOH | H |
| 17 | i-Pr | Cl | Cl | Et | H | COOH | H |
| 18 | i-Pr | Br | Br | Et | H | COOH | H |
| 19 | i-Pr | Cl | Cl | n-Pr | H | COOH | H |
| 20 | i-Pr | Br | Br | n-Pr | H | COOH | H |
| 21 | Br | Cl | Cl | Me | H | COOH | H |
| 22 | Me | Br | Br | Me | H | COOH | H |
| 23 | n-Bu | Cl | Cl | Me | H | COOH | H |
| 24 | ⌇cyclopropyl⌇ | Cl | Cl | Me | H | COOH | H |
| 25 | i-Pr | Cl | Cl | Me | Me | COOH | H |
| 26 | i-Pr | Br | Br | Me | Me | COOH | H |
| 27 | i-Pr | Cl | Cl | Me | H | COOEt | H |
| 28 | i-Pr | Br | Br | Me | H | COOEt | H |
| 29 | i-Pr | Cl | Cl | Me | H | COOH | Acetyl |

What is claimed is:
1. A compound of the formula wherein
X is oxygen (—O—), sulfur (—S—), carbonyl (—CO—), methylene (—$CH_2$—), or disubstituted nitrogen (—NH—);
$R_1$ is halogen, trifluoromethyl, or alkyl of 1 to 6 carbons or cycloalkyl of 3 to 7 carbons;
$R_2$ and $R_3$ are the same or different and are hydrogen, halogen, alkyl of 1 to 4 carbons or cycloalkyl of 3 to 6 carbons, at least one of $R_2$ and $R_3$ being other than hydrogen;

$R_4$ is methyl, ethyl, n-propyl or trifluoromethyl;

$R_5$ is hydrogen or lower alkyl;

$R_6$ is carboxylic acid, or ester thereof, or a prodrug thereof;

$R_7$ is hydrogen, or an alkanoyl or aroyl group, or other group capable of bioconversion to generate the free phenol structure (wherein $R_7$=H);

including all stereoisomers thereof, a prodrug thereof, or a pharmaceutically acceptable salt thereof.

2. The compound as defined in claim 1 wherein X is oxygen.

3. The compound as defined in claim 2 wherein $R_5$ is hydrogen.

4. The compound as defined in claim 3 wherein $R_1$ is isopropyl.

5. The compound as defined in claim 3 wherein $R_2$ and $R_3$ are each independently halogen.

6. The compound as defined in claim 3 wherein $R_2$ and $R_3$ are each independently an alkyl group.

7. The compound as defined in claim 3 wherein one of $R_2$ and $R_3$ is halogen and the other is an alkyl group.

8. The compound as defined in claim 3 wherein one of $R_2$ and $R_3$ is halogen and the other is hydrogen.

9. The compound as defined in claim 3 wherein one of $R_2$ and $R_3$ is alkyl and the other is hydrogen.

10. The compound as defined in claim 3 wherein $R_2$ and $R_3$ are independently Cl, Br, methyl or ethyl.

11. The compound as defined in claim 3 wherein $R_4$ is trifluoromethyl or methyl.

12. The compound as defined in claim 3 wherein $R_4$ is methyl.

13. The compound as defined in claim 1 wherein

X=O;

$R_1$ is halogen, trifluoromethyl, or alkyl of 1 to 6 carbons;

$R_2$ and $R_3$ are independently bromo, chloro or methyl;

$R_4$ is methyl or trifluoromethyl;

$R_5$ is hydrogen;

$R_6$ is carboxyl; and $R_7$ is hydrogen.

14. The compound as defined in claim 13 wherein $R_1$ is alkyl of 1 to 6 carbons.

15. The compound as defined in claim 3 having the structure

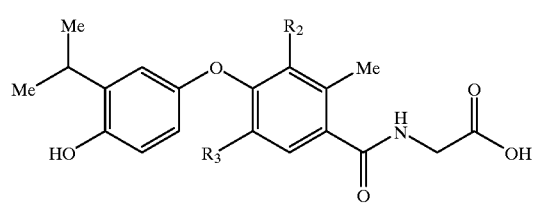

or

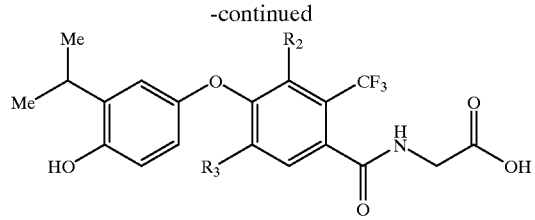

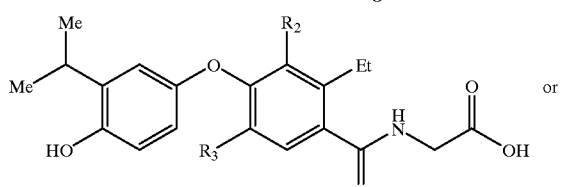

or

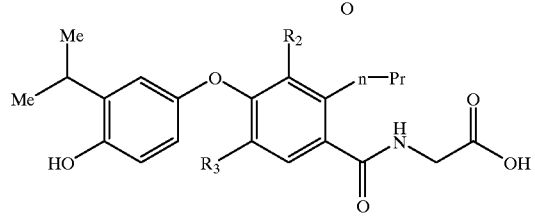

or an alkyl ester thereof.

16. The compound as defined in claim 1 having the structure

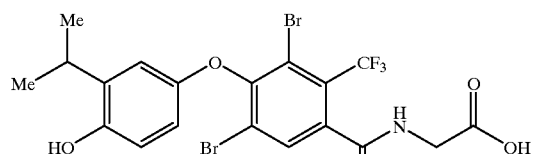

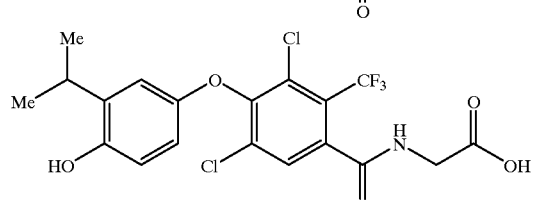

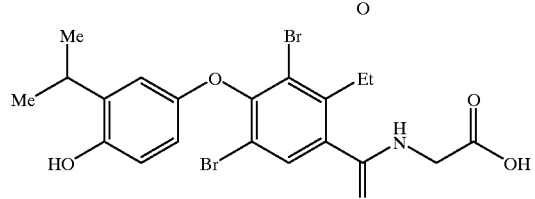

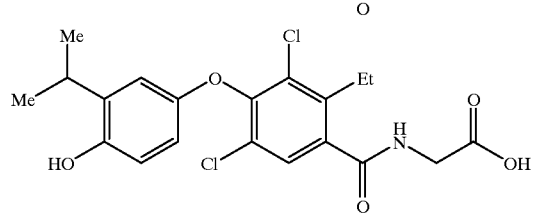

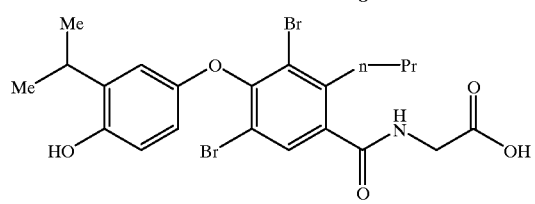

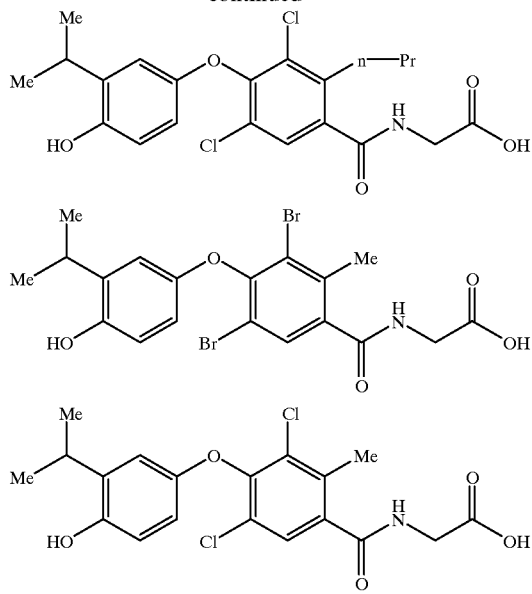

or or an alkyl ester thereof.

17. The compound as defined in claim 1 having the structure

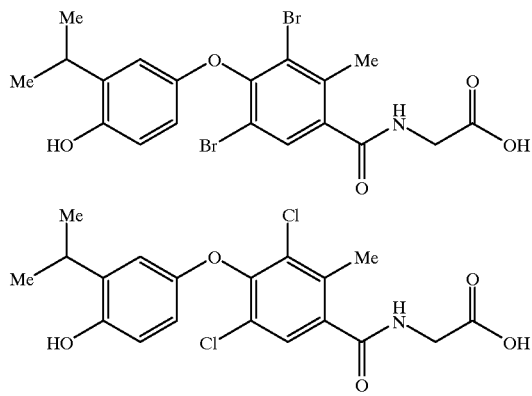

or an alkyl ester thereof.

18. The compound as defined in claim 1 which is

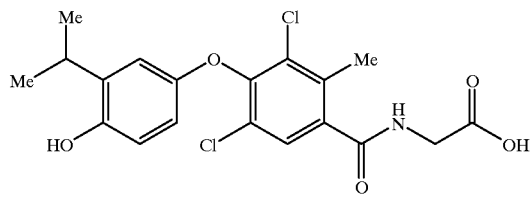

19. A method for preventing, inhibiting or treating a disease associated with metabolism dysfunction, or which is dependent on the expression of a $T_3$ regulated gene, which comprises administering to a patient in need of treatment a therapeutically effective amount of a compound as defined in claim 1.

20. The method as defined in claim 19 wherein the disease associated with metabolism dysfunction or which is dependent on the expression of a $T_3$ regulated gene is obesity, hypercholesterolemia, atherosclerosis, depression, osteoporosis, hypothyroidism, goiter, thyroid cancer, glaucoma, cardiac arrhythmia, congestive heart failure, or a skin disorder or disease.

21. A pharmaceutical composition comprising an effective amount of a compound according to claim 1 or a pharmaceutically acceptable salt thereof, together with a pharmaceutically acceptable carrier.

22. The method according to claim 20 in which the skin disorder or disease is dermal atrophy, post surgical bruising caused by laser resurfacing, keloids, stria, cellulite, roughened skin, actinic skin damage, lichen planus, ichtyosis, acne, psoriasis, Dernier's disease, eczema, atopic dermatitis, chloracne, pityriasis and skin scarring.

23. A method to treat skin disorder or disease by the use of a compound of claim 1 in combination with a retinoid or a vitamin D analog.

24. A pharmaceutical combination comprising a compound as defined in claim 1 and a hypolipidemic agent, an antidiabetic agent, an antidepressant, a bone resorption inhibitor, an appetite suppressant and/or an anti-obesity agent.

25. The combination as defined in claim 24 wherein the hypolipidemic agent is a thiazolidinedione, an MTP inhibitor, a squalene synthetase inhibitor, an HMG CoA reductase inhibitor, a fibric acid derivative, an ACAT inhibitor, a cholesterol absorption inhibitor, an ileal $Na^+$/bile cotransporter inhibitor, a bile acid sequestrant and/or nicotinic acid or a derivative thereof.

26. The combination as defined in claim 24 wherein the hypolipidemic agent is pravastatin, simvastatin, lovastatin, atorvastatin, fluvastatin or cerivastatin.

27. The combination as defined in claim 24 wherein the compound is present in a weight ratio to the hypolipidemic agent or antidiabetic agent within the range from about 0.01:1 to about 300:1.

28. The combination as defined in claim 24, wherein the antidiabetic agent is a biguanide, a sulfonylurea, a glucosidase inhibitor, a thiazolidinedione, an insulin sensitizer, a glucagon-like peptide-1 (GLP-1) or insulin.

29. The combination as defined in claim 28 wherein the antidiabetic agent is metformin, glyburide, glimepiride, glipyride, glipizide, chlorpropamide, gliclazide, acarbose, miglitol, troglitazone, pioglitazone, rosiglitazone, and/or insulin.

* * * * *